US006664309B2

(12) United States Patent
Svenningsen et al.

(10) Patent No.: US 6,664,309 B2
(45) Date of Patent: Dec. 16, 2003

(54) ANTIMICROBIAL HOT MELT ADHESIVE

(75) Inventors: Lacretia Svenningsen, Wauwatosa, WI (US); Diane Strelow, Waukesha, WI (US); Mark Alper, Mukwonago, WI (US); Marihelen Hoppa-Willbrandt, Cedarburg, WI (US)

(73) Assignee: Bostik Findley, Inc., Wauwatosa, WI (US)

( * ) Notice: Subject to any disclaimer, the term of this patent is extended or adjusted under 35 U.S.C. 154(b) by 214 days.

(21) Appl. No.: 09/732,378

(22) Filed: Dec. 7, 2000

(65) Prior Publication Data

US 2002/0115744 A1 Aug. 22, 2002

(51) Int. Cl.[7] .............................. C08K 5/09; C08K 5/10; C08K 5/12; C08K 5/13
(52) U.S. Cl. ..................... 523/122; 524/291; 524/343; 524/487
(58) Field of Search .................. 524/291, 343, 524/487; 523/122

(56) References Cited

U.S. PATENT DOCUMENTS

| 2,137,169 A | 11/1938 | Levey ...................... 167/84 |
| 3,249,109 A | 5/1966 | Maeth et al. ............... 128/268 |
| 3,506,720 A | 4/1970 | Model et al. ............... 260/613 |
| 3,632,740 A | 1/1972 | Robinson et al. ............ 424/28 |
| 3,734,097 A | 5/1973 | Zaffaroni .................. 128/268 |
| 3,769,071 A | 10/1973 | Trancik .................... 117/112 |
| 3,896,789 A | 7/1975 | Trancik .................... 128/2 |
| 4,073,291 A | 2/1978 | Marvel et al. .............. 128/155 |
| 4,310,509 A | 1/1982 | Berglund et al. ............ 424/28 |
| 4,323,557 A | 4/1982 | Rosso et al. ............... 424/28 |
| 5,069,907 A | 12/1991 | Mixon et al. ............... 424/445 |
| 5,829,442 A | 11/1998 | Cox et al. ................. 128/849 |
| 6,146,654 A | 11/2000 | Kubo ....................... 424/443 |
| 6,216,699 B1 | 4/2001 | Cox et al. ................. 128/849 |

FOREIGN PATENT DOCUMENTS

| EP | 0800833 | 10/1997 |
| EP | 0812893 | 12/1997 |
| EP | 1029448 | 8/2000 |
| GB | 2030860 | 4/1980 |
| WO | WO97/48779 | 12/1997 |

Primary Examiner—Kriellion A. Sanders
(74) Attorney, Agent, or Firm—Andrus, Sceales, Starke & Sawall, LLP

(57) ABSTRACT

Hot melt adhesive compositions suitable for a variety of applications, especially in nonwoven disposable articles, are prepared by blending various adhesive components with a bacteriostat. The bacteriostat is incorporated into the adhesive compositions in sufficient amounts to inhibit the growth of various microorganisms, particularly bacteria. The preferred bacteriostat is triclosan in amounts of 0.01% to 5% by weight.

54 Claims, 3 Drawing Sheets

ANTIMICROBIAL HOT MELT ADHESIVE

BACKGROUND OF THE INVENTION

The present invention relates to hot melt adhesives, and more specifically to hot melt adhesives having antimicrobial properties and which find usefulness in the manufacture of disposable nonwoven articles.

Nonwoven fabric is comprised of an interlocking fiber network, and is employed in the construction of disposable goods. Specific applications of nonwovens have included disposable diapers, sanitary napkins, surgical drapes, hospital pads and adult incontinence products.

In such applications it is generally necessary to adhere nonwoven, tissue, absorbent fluff or the like to another substrate. This second substrate may be another nonwoven fabric, tissue, or a material such as a polyolefin e.g. a polyethylene or polypropylene layer. Typically, a hot melt adhesive has been used to bond such materials together since there is no evaporation step necessary during manufacture, as would be the case for water-based or solvent-based adhesives. Suitable hot melt adhesives must possess the appropriate bond strength to adhere the substrates involved, and must also possess good flexibility, no staining or bleed through, suitable viscosity and open time to function on commercial equipment, acceptable stability under storage conditions, and acceptable thermal stability under normal application conditions.

Many different polymers have been used in hot melt adhesives employed in the construction of disposable nonwoven goods. In this regard typical hot melt adhesives have employed polymers which have included polybutene-1 (homopolymer and copolymer); S-I-S (styrene-isoprene-styrene) block copolymer; SBS (styrene-butadiene-styrene) block copolymer; SEBS (styrene-ethylene-butylene-styrene) block copolymer; EVA (ethylene vinyl acetate); and APAO (amorphous poly alpha olefin). These polymers, when properly blended, provide acceptable adhesion between most substrates employed in typical nonwoven construction such as diapers.

One noteworthy concern of prior hot melt adhesives used in the above-noted nonwoven applications is the lack of protection against the direct or indirect effects by microorganisms which could change the properties, appearance or odor of the adhesive and/or nonwoven article. Therefore, it would be desirable to have a hot melt adhesive which is useful for bonding to substrates which are typically employed in the construction of nonwoven articles, such as polyethylene, polypropylene, nonwoven, tissue, or fluff, and which further provides hygienic properties by inhibiting or preventing growth of bacteria which often is accompanied by a change in adhesion properties, color formation and odor development.

SUMMARY OF THE INVENTION

It is therefore an object of the present invention to provide an improved hot melt adhesive which is useful for the manufacture of disposable nonwoven articles.

A further object of the present invention is to provide a hot melt adhesive which can be employed as a construction adhesive which further provides hygienic properties to disposable nonwoven articles.

In order to accomplish the above objects, the present invention provides a hot melt adhesive having the following composition (by weight):

about 10–80% of a polymer;
about 20–70% of a tackifying resin;
about 0–50% of a plasticizer;
about 0–50% of a wax;
about 0.1–5% of an antioxidant; and
about 0.01–5% of a bacteriostat, the components totaling 100% by weight.

The bacteriostat must be reasonably compatible with the other raw materials used in the hot melt adhesive so that it does not adversely affect the construction performance or the thermal stability of the adhesive. The bacteriostat also should not contain any water or other solvents so that it is readily processable in hot melt mixing equipment, and also should be non-toxic for the end user.

Such criteria is accomplished by the incorporating into an adhesive a compound of the formula:

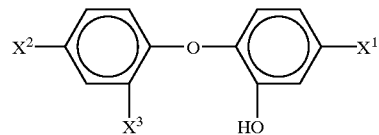

wherein $X^1$ is a member selected from the group consisting of chlorine and bromine, $X^2$ is a member selected from the group consisting of chlorine and bromine, and $X^3$ is a member selected from the group consisting of hydrogen and chlorine. When each of $X^1$, $X^2$ and $X^3$ represents chlorine, the compound is triclosan, which is the preferred bacteriostat.

The adhesives of the instant invention thus provide excellent growth-inhibiting action against bacteria, and are especially suited for use in absorbent products such as diapers, training pants, incontinent products, feminine care products, and medical products. With all of these products there is a need to bond the layers or substrates of the article together and hot melts are often used as discussed above. Usually the core area of the article is adhered by spraying a layer of adhesive onto a nonwoven substrate and adhering it to an absorbent core. In many cases, a layer of tissue is placed between the nonwoven and the core, sometimes fully wrapping the core and in other cases simply covering the top or bottom layer. Another layer of adhesive may be used to bond the absorbent core fluff to the tissue and further another layer of adhesive may bond the tissue or fluff to the backsheet (which is often polyethylene or a composite laminate). So there is at least one and often a number of layers of sprayed hot melt used in bonding the core into place, and these multiple layers of adhesive, all or any combination of which may contain the bacteriostat ingredient, provide an excellent environment in which microorganisms, and particularly bacteria, may be controlled.

In another aspect of the invention, there is provided an antimicrobial, sprayable, thermoplastic polymer composition comprising a blend of about 95–99.99% by weight of a thermoplastic polymer, said thermoplastic polymer having a melt index greater than about 100, and about 0.01–5% by weight of a bacteriostat, and where the composition has a viscosity of less than about 50,000 cP at 350° F. Preferably, the polymer has a melt index greater than about 500, and the composition has a viscosity less than about 20,000 cP. Most preferably, the polymer has a melt index greater than about 1,000, and the composition has a viscosity less than about 10,000 cP. For certain applications and/or desired end uses, there may be no need to blend a tackifying resin, plasticizer, wax or antioxidant with the polymer. This depends upon the inherent properties of the polymer, the desired end use, and other factors typically considered by those skilled in the art.

DETAILED DESCRIPTION OF THE INVENTION

Figure 1:
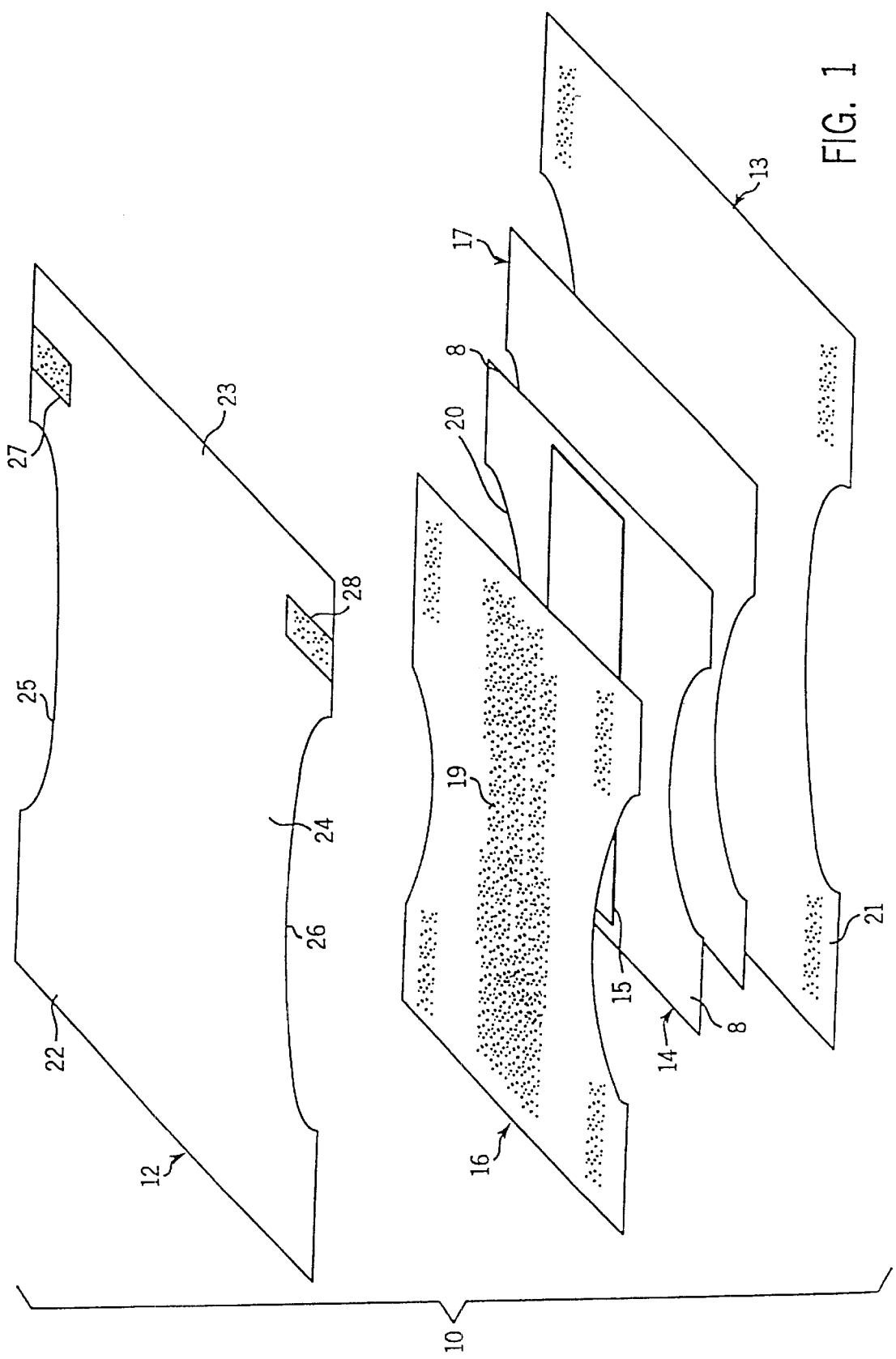
FIG. 1 is a schematic, exploded, perspective view of a disposable diaper incorporating a hot melt adhesive constructed in accordance with the present invention.

A hot melt adhesive composition having ingredients in the following ranges provides advantages over current technology when evaluated for the control of microorganisms, particularly bacteria. More particularly, the adhesive composition of the present invention has the following ingredients by weight;

about 10–80% of a polymer;
about 20–70% of a tackifying resin;
about 0–50% of a plasticizer;
about 0–50% of a wax;
about 0.1–5% of an antioxidant; and
about 0.01–5% of a bacteriostat, the components totaling 100% by weight.

In another aspect of the invention, there is provided an antimicrobial, sprayable, thermoplastic polymer composition comprising a blend of about 95–99.99% by weight of a thermoplastic polymer, said thermoplastic polymer having a melt index greater than about 100, and about 0.01–5% by weight of a bacteriostat, and where the composition has a viscosity of less than about 50,000 cP at 350° F. Preferably, the polymer has a melt index greater than about 500, and the composition has a viscosity less than about 20,000 cP. Most preferably, the polymer has a melt index greater than about 1,000, and the composition has a viscosity less than about 10,000 cP.

Any of a variety of available thermoplastic materials can be used, either alone or as a blend, as the polymer ingredient in the compositions of the invention. With respect to the adhesive composition, the polymer may be present in an amount from about 10% to about 80% by weight, preferably from about 15% to about 45%, and most preferably from about 20% to about 35%. With respect to the polymer composition, the polymer may be present in an amount from about 95% to about 99.99% by weight. Examples of such thermoplastic materials include ethylene based polymers, including ethylene/vinyl acetate (EVA), ethylene acrylate, ethylene methacrylate, ethylene methyl acrylate, ethylene methyl methacrylate, high and low density polyethylene, polyethylene blends and chemically modified polyethylene, copolymers of ethylene and 1–6 mono- or di-unsaturated monomers, ethylene/styrene interpolymers (ESI), polyesters such as sulfonated polyesters; amorphous polyalphaolefins (APAOs), including atactic polypropylene, and others; metallocene catalyzed polyalphaolefins; SIS (styrene-isoprene-styrene) block copolymer; SBS (styrene-butadiene-styrene) block copolymer; SEBS (styrene-ethylene-butylene-styrene) block copolymer; SBR (styrene-butadiene-rubber); acrylic polymers and copolymers; as well as styrene acrylic polymers and copolymers; polybutene-1 homopolymers and copolymers, commonly referred to as polybutylene, linear A-B-A block, linear A-(B-A)$_n$-B multiblock copolymers, and radial or teleblock copolymers of the formula (A-B)$_n$-Y wherein A comprises a polystyrene block, B comprises a substantially rubbery polybutadiene or polyisoprene block, Y comprises a multivalent compound, and n is an integer of at least 3. The midblocks can be post-treated to improve their heat stability through hydrogenation or other post-treatment removing residual unsaturation. The size and the amount of the A or end blocks in the A-B-A block copolymer structure may be as much as 14–51 wt-% of the polymer.

In addition, water soluble polymers may also be employed as the thermoplastic material. Common water soluble polymers include polyesters such as sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, and polyvinylpyrrolidone/vinyl acetate. Other water soluble polymers may be used depending upon the desired end use and properties of the polymer, and thus the above list should neither be considered all-inclusive nor limiting on the scope of the term "thermoplastic material" or "thermoplastic polymer" as used herein.

Preferred thermoplastic polymers for use in the compositions of this invention are ethylene-vinyl-acetate (EVA), styrene-isoprene-styrerie (SIS) block copolymer, styrene-butadiene-styrene (SBS) block copolymer, styrene-ethylene-butylene-styrene (SEBS) block copolymer, high density and low density polyethylene, polyethylene blends and chemically modified polyethylene, sulfonated polyesters, amorphous polyalphaolefins especially atactic polypropylene (atactic PP), ethylene/styrene interpolymers (ESI), metallocene catalyzed APAOs, polyvinyl methyl ether, and polyethylene glycol polymers.

While the total styrene content of the polymers can be as much as 51 wt-% of the polymer, and since the polymers can have more than two A blocks for optimal performance, the total A block should be less than or equal to about 45 wt-% of the polymers, and, most preferably, is less than or equal to 35 wt-% of the polymer. In an S-B-S (styrene-butadiene-styrene) copolymer, the preferred molecular weight is about 50,000 to 120,000, and the preferred styrene content is about 20 to 45 wt-%. In an S-I-S (styrene-isoprene-styrene) copolymer, the preferred molecular weight is about 100,000 to 250,000 and the preferred styrene content is about 14–35 wt-%. Hydrogenating the butadiene midblocks produces rubbery midblocks that are typically considered to ethylene-butylene midblocks.

Such block copolymers are available from Shell Chemical Company, Enichem Elastomers Americas, Inc. and Dexco Polymers. Multiblock or tapered block copolymers (the A-(B-A)n-B type) are available from Firestone.

The tackifying resins which are used in the hot melt construction adhesives of the present invention are those which extend the adhesive properties and improve the specific adhesion of the polymer. As used herein, the term "tackifying resin" includes:

(a) natural and modified rosin such as, for example, gum rosin, wood rosin, tall-oil rosin, distilled rosin, hydrogenated rosin, dimerized rosin and polymerized rosin;

(b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin;

(c) polyterpene resins having a softening point, as determined by ASTM method E28-58T, of from about 20° C. to 140° C., the latter polyterpene resins generally resulting from the polymerization of terpene hydrocarbons, such as the monoterpene known as pinene, in the presence of Friedel-Crafts catalysts at moderately low temperatures; also included are the hydrogenated polyterpene resins;

(d) copolymers and terpolymers of natural terpenes, e.g. styrene/terpene, α-methyl styrene/terpene and vinyl toluene/terpene;

(e) phenolic-modified terpene resins such as, for example, the resin product resulting from the condensation, in an acidic medium, of a terpene and a phenol;

(f) aliphatic petroleum hydrocarbon resins having Ring and Ball softening points of from about 10° C. to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Goodyear Tire and Rubber Company;

(g) aromatic petroleum hydrocarbons and the hydrogenated derivatives thereof;

(h) aliphatic/aromatic petroleum derived hydrocarbons and the hydrogenated derivatives thereof.

Mixtures of two or more of the above described tackifying resins may be required for some formulations. Although a range of 20–70% by weight tackifying resin may be used, the preferred range is 35% to 60% and the most preferred range is 45% to 60%. An example of a commercially available tackifying resin which is useful for the present invention includes the resin which is identified commercially by the trade designation Unitac R100L. This resin is a pentaerythritol based tall-oil rosin ester, and is available from Union Camp.

Commercially available polymerized rosins may be secured from Arizona Chemical Company under the trade designations "Sylvatac 295, RX, R85, 95, and 140," respectively. Additionally, Hercules, Inc. produces a suitable dimerized rosin under the trade designation "Dymerex." Commercially suitable partially hydrogenated rosins may be secured from Hercules, Inc. under the trade designations "Foral AX" and "Stabelite." Finally, partial ester of dibasic modified tall oil rosins may be secured from Arizona Chemical Company under the trade designation "Sylvatac 203," and "Beckacite 4901." Both water soluble and water insoluble plasticizers can be present in the composition of the present invention either alone or in any desired combination in amounts of about 0% to about 50% by weight, preferably from about 5% to about 40% by weight, and most preferably from about 20% to about 35% by weight, in order to provide desired viscosity control without substantially decreasing the adhesive strength or the service temperature of the adhesive. Both liquid and solid plasticizers can be used in the composition of the present invention.

The water soluble plasticizers used herein comprise low molecular weight polyethylene glycols, multifunctional alcohol and the general class of surfactants wherein the molecules contain both a hydrophilic group and a hydrophobic group. The hydrophilic group of the molecule generally consists, of, but is not limited to, polyethylene glycol, polypropylene glycol, a mono- or di-hydroxylated amino group, an ethoxylated amino radical, polyalkylene glycol esters of carboxylic group, substituted or unsubstituted glycerol, glucose, sucrose and sorbitan groups. The hydrophobic group of the molecule generally consists of, but is not limited to, a hydrocarbon radical such as, alkylphenol groups, dialkyl phenol groups, or a linear or branched aliphatic radicals. The preferred soluble plasticizers include ethoxylated alkyphenols, ethoxylated fatty acids and ethoxylated fatty alcohol having a HLB value in the range of 8.0–20.0. An ethoxylated alkyphenol with HLB value of 13.5 can be obtained under the trade designation Triton X-100 from Union Carbide Corporation of Danbury, Conn., and water soluble ethoxylated fatty acids, such as polyethylene glycol 600 monolaurate (HLB=14.6) and polyethylene glycol 1000 dilaurate (HLB=14.2), can be purchased from Stepan Company of Northfield, Ill. under the trade designations of Kessco PEG 600MC and PEG 1000DL, respectively.

A suitable insoluble plasticizer may be selected from the group which includes dipropylene glycol dibenzoate, pentaerythritol tetrabenzoate; polyethylene glycol 400-di-2-ethylhexoate; 2-ethylhexyl diphenyl phsophate; butyl benzyl phthalate, dibutyl phthalate, dioctyl phthalate, various substituted citrates, and glycerates. Suitable dipropylene glycol dibenzoate and pentaerythritol tetrabenzoate may be purchased from Velsicol Chemical Company of Chicago, Ill. under the trade designations "Benzoflex 9-88 and S-552", respectively. Further, a suitable polyethylene glycol 400-di-2-ethylhexoate may be purchased from C.P. Hall Company of Chicago, Ill. under the trade designation "Tegmer 809". A suitable 2-ethylhexyl diphenyl phosphate, and a, butyl benzyl phthalate may be purchased from Monsanto Industrial Chemical Company of St. Louis, Mo. under the trade designation "Santicizer 141 and 160", respectively.

A suitable plasticizer may be selected from the group which not only includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof. The plasticizer that finds usefulness in the present invention can be any number of different plasticizers but the inventors have discovered that mineral oil such as Kaydol manufactured by Witco, is particularly useful in the present invention. Benzoflex 9-88, a dipropylene glycol dibenzoate manufactured by Velsicol, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications).

Waxes in the composition of the present invention can be present either alone or in any desired blend in amounts of about 0% to about 50% by weight, preferably from about 5% to about 40% by weight, and most preferably from about 10% to about 30% by weight, and are used to reduce the melt viscosity and surface tack of the hot melt construction adhesives without appreciably decreasing their adhesive bonding characteristics. These waxes also are used to reduce the open time of the composition without effecting the temperature performance. Among the useful waxes are:

(1) low molecular weight, that is, 600–6000 ($\overline{Mn}$), polyethylene having a hardness value, as determined by ASTM method D-1321, of from about 0.1 to 120 and ASTM softening points of from about 150° to 250° F.;

(2) petroleum waxes such as paraffin wax having a melting point of from about 130° to 170° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) synthetic waxes made by polymerizing carbon monoxide and hydrogen such as Fischer-Tropsch wax; and (5) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred to use in the compositions of the present invention have a Ring and Ball softening point of 200° F. to 350° F. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent.

The present invention includes a stabilizer or antioxidant in an amount of from about 0.1% to about 5% by weight, but preferably from about 0.1% to about 3%, and most preferably about 0.1% to 2%. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant is Irganox 1010, a tetrakis (methylene(3,5-di-teri-butyl-4-hydroxyhydrocinnamate)) methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl) benzene;

pentaerythritol tetrakis-3(3,5-di-tert-butyl-4-hydroxyphenyl) propionate;

n-octadecyl-3(3,5-ditert-butyl-4-hydroxyphenyl) propionate;

4,4'-methylenebis(4-methyl-6-tert butylphenol);

4,4'-thiobis(6-tert-butyl-o-cresol);

2,6-di-tert-butylphenol;

6-(4-hydroxyphenoxy)-2,4-bis(n-ocytlthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

The performance of these stabilizers may be further enhanced by utilizing, in conjunction therewith: (1) synergists such as, for example, thiodipropionate esters and phosphites; and (2) chelating agents and metal deactivators as, for example, ethylenediaminetetraacetic acid, salts thereof, and disalicylalpropylenediimine.

A bacteria growth-inhibiting amount of about 0.01% to about 5% by weight, preferably about 0.1% to about 4% by weight, and most preferably about 0.3% to about 2% by weight, of a bacteriostat is also incorporated into the present adhesive composition. The bacteriostat can be present alone or in any desired blend, and functions to control and/or inhibit the growth of microorganisms, particularly bacteria, on and near the adhesive itself as well as on one or more of the substrate or substrates bonded together by the adhesive. Typical bacteriostats are benzoates, phenols, aldehydes, halogen containing compounds, nitrogen compounds, and metal-containing compounds such as mercurials, zinc compounds and tin compounds. The preferred bacteriostat is a compound of the formula:

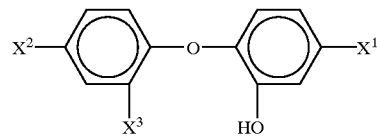

wherein $X^1$ is a member selected from the group consisting of chlorine and bromine, $X^2$ is a member selected from the group consisting of chlorine and bromine, and $X^3$ is a member selected from the group consisting of hydrogen and chlorine. When each of $X^1$, $X^2$ and $X^3$ represents chlorine, the compound is triclosan, which is the preferred bacteriostat. Compounds of the above type are disclosed in U.S. Pat. No. 3,506,720 along with a method of synthesizing such compounds.

Triclosan has the chemical name of 2,4,4'-trichloro-2'-hydroxy-diphenyl-ether, which is available under the trade name "Irgasan PA" from Ciba Specialty Chemicals Corporation.

The bacteriostat should be effective both against gram positive as well as gram negative bacteria. Thus, the bacteriostat should have a growth-inhibiting action at a minimum on at least one of the following grain positive and gram negative bacteria: *Staphylococcus aureus, Escherichia coli, Bacillus subtilis, Klebsiella pneumoniae, Salmonella pullorum, Salmonella typhi, Salmonella paratyphi* A and B, *Salmonella typhimurium, Salmonella enteritidis, Shigella dysenteriae, Shigella flexneri, Proteus mirabilis,* or *Serratia marcescens*.

The bacteriostat should also advantageously be colorless or have only slight inherent color. This property enables the bacteriostat to be used in adhesives in absorbent articles, particularly disposable diapers, for which it is not possible to use strongly colored known bactericidal compounds. In addition, the bacteriostat should be odorless, stable in hot melt adhesives and non-toxic.

The above-identified bacteriostats are typically not soluble in water, but are soluble in most organic solvents. As a result, these bacteriostats are ideal for use in disposable absorbent articles, especially diapers, since they will not dissolve in urine or other body fluids. Also, because of their solubility, they can be readily incorporated into hot melt adhesives for combating microorganisms. Preferably, the bacteriostat has a low melting point of less than 100° C. for ease of compounding, and has low volatility as measured by a vapor pressure of less than about $5 \times 10^{-5}$ mm of mercury at 20° C. They can thus be incorporated directly into the adhesive using conventional mixing equipment.

Fillers may also be incorporated into the adhesive composition in amounts ranging from about 0% to 80% by weight, preferably about 0% to 50% by weight, and most preferably about 0% to 10% by weight. These are inert in the formulation, and are typically added as an anti-blocking agent. Fillers may include talc, clay, alumina, hydrated alumina ($Al_2O_3$—$3H_2O$), silicates such as magnesium silicates, aluminum silicates, sodium silicates, and potassium silicates as well as, mica, calcium carbonate ($CaCO_3$), silica, wollastonite, feldspar, glass microspheres, ceramic microspheres, thermoplastic microspheres, baryte and wood flour. Other commonly employed fillers may also be used as long as they do not materially alter the function of the remaining ingredients in the formulation.

Optional conditioning additives may be incorporated into the adhesive composition in amounts of from about 0% to 30% by weight, preferably from about 0.1% to 15%, and most preferably from about 2% to 10%, in order to modify particular physical properties. These additives may include colorants, such as titanium dioxide, fluorescent agents, surfactants, and the like.

The surfactant can optionally be present in the composition of the present invention in amounts of from about 0% to about 30% by weight, and preferably from about 0.1% to 15% by weight and most preferably from about 2% to about 10% in order to make the adhesive more hydrophilic. The surfactant has a hydrophile-lipophile balance (HLB) number of less than 15, and is incorporated into the composition in an amount such that the resultant adhesive has a contact angle of 75° or less, and preferably less than about 40°. A low contact angle is desirable so that water, urine or other water-based discharges "wet out" rather than "bead up" resulting in the fluid being directed away from the adhesive.

The HLB of a surfactant is an expression of its hydrophile-lipophile balance, i.e. the balance of the size and strength of the hydrophilic (water-loving or polar) and the lipophilic (oil-loving or non-polar) groups of the surfactant. All surfactants consist of a molecule that combines both hydrophilic and lipophilic groups.

The surfactant must be reasonably compatible with the other raw materials used in the hot melt adhesive so that it does not adversely affect the construction performance of the adhesive. On the other hand, the surfactant must "bloom" to the surface of the adhesive so as to lower the contact angle and make the adhesive more hydrophilic. Thus, a delicate balance of compatibility must be maintained. The surfactant also should not contain any water or other solvents making it processable in hot melt mixing equipment and non-toxic for the end user. The surfactant also must be sufficiently stable and non-volatile to allow processing in hot melt manufacturing and application equipment without effect on the adhesive.

As used herein, the term "surfactant" or "surface-active agent" refers to any compound that reduces surface tension when dissolved in water or water solutions, or which reduces interfacial tension between two liquids, or between a liquid and a solid. Examples of suitable surfactants include, but are not limited to, the following:

(1) Fatty acid esters such as glycerol esters, PEG esters, and sorbitan esters, including ethylene glycol distearate, ethylene glycol monostearate, glycerol mono and/or dioleate, PEG dioleate, PEG monolaurate, sorbitan monolaurate, sorbitan trioleate, etc. These surfactants are available from ICI, Rhone-Poulenc, and other sources.

(2) Nonionic ethoxylates such as alkylphenol ethoxylates, alcohol ethoxylates, alkylamine ethoxylates, etc., including octylphenol ethoxylate, nonylphenol ethoxylate, alkylamine ethoxylates, etc. These surfactants are available from Rhone-Poulene, Union Carbide, and other sources.

(3) Nonionic surfactants such as 2,4,7,9-tetramethyl-5-decyn-4,7-diol available from Air Products.

(4) Ethylene oxide/Propylene oxide copolymers which are available from Union Carbide, BASF, etc. It should be noted that these and other surfactants can be blended if necessary to produce the best blend of hydrophilic performance properties.

Atmer 688, a nonionic surfactant blend, and Alkamuls GMS/C a glycerol monostearate, both manufactured by ICI Americas, Inc. have been found to be preferred surfactants for use in the present adhesive composition.

Contact angle measurements of liquid droplets on substrate surfaces are used to characterize surface wettability. The lower the contact angle, the more hydrophilic is the adhesive. The contact angle is defined as the angle between the substrate support surface and the tangent line at the point of contact of the liquid droplet with the substrate. The value of the contact angle of the liquid droplet will depend upon the surface energy of the substrate and the surface tension of the liquid. If complete wetting takes place between the liquid and the substrate surface, the droplet will spread out over the substrate and contact angle will approach zero, whereas if the wetting is only partial, the resulting contact angle will lie in the range of 0 to 180 degrees. The contact angles may be obtained utilizing a model CAM-FILM contact angle meter available from Tantec, Inc. using the half-angle measuring method described in U.S. Pat. No. 5,268,733.

The hot melt adhesive composition of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

The adhesives may be used in manufacturing of toilet tissues, paper towels, wipes and other consumer products, particularly absorbent articles such as disposable diapers, as the laminating adhesive to bind a plurality of substrate layers.

The adhesives of the present invention, in both pressure sensitive and nonpressure sensitive forms, are also useful in assembly or constructions of food packaging to bind a substrate composed of plastic film, paper, metal foil or the like to another substrate. This second substrate may be another plastic film, paper, or metal foil. The plastic material may be, for example, polyethylene or polypropylene film.

The adhesives of the present invention can be coated or applied with a variety of application techniques known in the art, which include, for example, slot die, spray, gravure, extrusion, application wheel, or other known application apparatus.

As used herein, the term "absorbent article" refers to a device or product which absorbs and contains body fluids and exudates such as urine. More specifically, this term refers to such devices or articles that are worn against or in proximity to the body of a wearer to absorb and contain various fluids and exudates discharged from the body. Examples of typical absorbent articles are disposable diapers, feminine care products such as sanitary napkins and pantyliners, and medical products, such as surgical drapes, and the like. As used herein, the term "diaper" refers to an absorbent article typically worn by infants, young children and adult incontinent persons. As readily understood, such an absorbent article is worn about the lower torso of the wearer and is held in place about the wearer's hips. The term "disposable" is used herein to describe absorbent articles which are to be discarded after a single use. Such articles are not intended to be laundered or otherwise re-used as an absorbent article. Preferred embodiments of absorbent articles of the present invention are diaper 10 schematically shown in FIGS. 1 and 2, and feminine care pad 11 schematically illustrated in FIG. 3.

Figure 2:
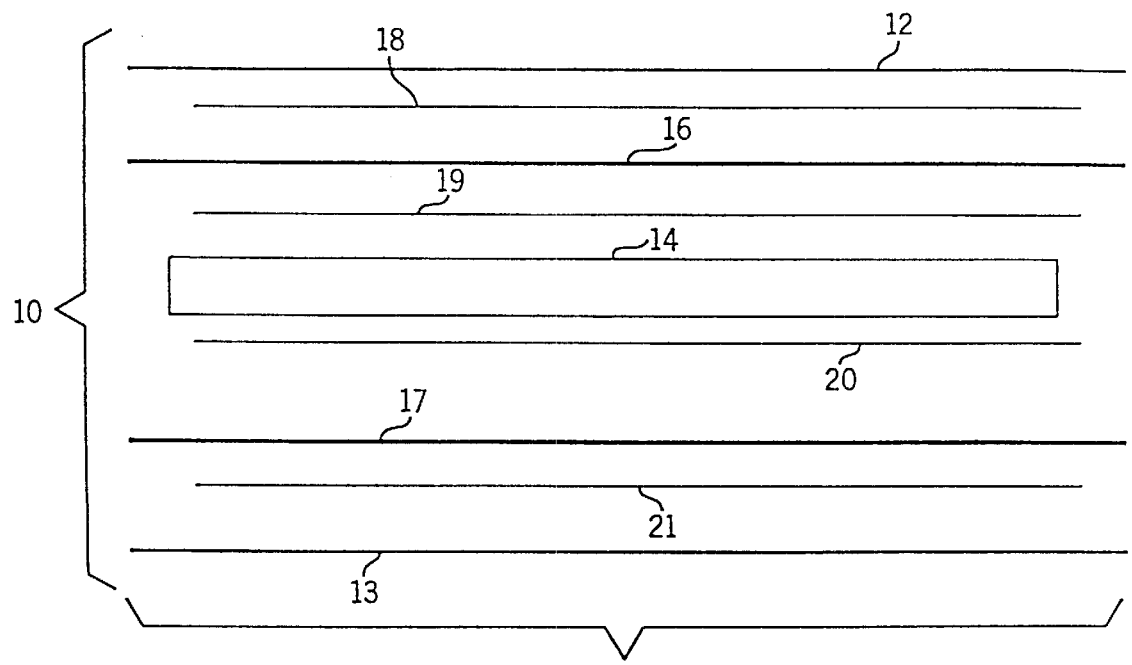
FIG. 2 is a schematic cross-sectional view of the diaper of FIG. 1.

Referring now to FIGS. 1 and 2 there is illustrated in FIG. 1 various substrates comprising diaper 10 in its flat, uncontracted state with portions of the structure being shown schematically to more clearly show the construction of diaper 10. FIG. 2 schematically illustrates in cross section the multiple layers or substrates of diaper 10.

As shown, diaper 10 comprises multiple layers of sheet material or substrates adhesively bonded together to form the absorbent article. More specifically, diaper 10 includes a fluid pervious nonwoven topsheet 12 and a fluid impervious backsheet 13 (typically composed of a polyolefin material such as polyethylene or polypropylene) joined with topsheet 12. An absorbent core 14 is positioned between topsheet 12 and backsheet 13. Absorbent core 14 may be comprised of fluff 8 and, optionally, a centrally disposed superabsorbent polymer (SAP) material 15. Fluff 8 is typically composed of absorbent fibers such as cellulose fibers, but may also include other absorbent natural or synthetic fibers and/or materials. Diaper 10 may also include a top tissue layer 16 disposed between topsheet 12 and core 14 as well as a bottom tissue layer 17 disposed between backsheet 13 and core 14. As shown best in FIG. 2, each substrate can be bonded to an adjacent substrate by a layer of an adhesive formulated in accordance with the present invention. For example, nonwoven topsheet 12 is bonded to top tissue layer 16 by a layer of adhesive 18 applied to the underside of topsheet 12. In turn, top tissue layer 16 is bonded to core 14 by a layer of adhesive 19. Core 14 is bonded to bottom tissue layer 17 by a layer of adhesive 20 and bottom tissue layer 17 in turn is bonded to a backsheet 13 by a layer of adhesive 21 applied to the upper surface of backsheet 13. The adhesive may be sprayed, spiral sprayed, melt blown, slot applied or may be applied as a bead depending upon the location and the type of bond desired. Thus, in one embodiment the adhesive of the present invention may be used as a conventional construction adhesive for absorbent articles. In another embodiment, the adhesive may be applied to selective locations of the absorbent article to function as a delivery system for the antimicrobial component so as to be effective in the desired location. In yet a third embodiment, it may be desirable to tailor the water solubility of the adhesive to provide a controlled rate of release for the antimicrobial component, at one or more specific locations of the absorbent article.

As noted above, the absorbent core 14 may contain discrete particles of a superabsorbent material. Superabsorbents are those materials which, upon contact with liquids such as water and body fluids, imbibe and retain such liquids and thereby form hydrogels. In this manner, liquids discharged into the absorbent core 14 can be acquired and held by the particles, thereby providing enhanced absorbent capacity and/or improved liquid retention performance.

The particles of superabsorbent material can be of any desired shape, e.g. spiral or semi-spiral, cubic, rod-like, polyhedral, spherical, etc. Shapes having a large greatest dimension/smallest dimension ratio, such as needles, flakes, and fibers, may also be used herein. Particles also include conglomerates of individual particles. Preferred superabsorbent materials for use in the present invention are "nonfibrous" particles such that the length to diameter ratio of the particulate material is about 10 or less, typically about 1 or less.

The superabsorbent can be an inorganic material such as a silica gel or an organic compound such as a cross-linked polymer. However, superabsorbent will generally comprise a substantially water-insoluble, slightly cross-linked, partially neutralized, hydrogel-forming polymer material. Such absorbent gelling materials can be prepared from unsaturated acid-containing monomers.

Suitable unsaturated acidic monomers for use in preparing the absorbent gelling materials used include those described in U.S. Pat. RE 32,649. Preferred monomers include acrylic acid, methacrylic acid, and 2-acrylamido-2-methyl propane sulfonic acid, with acrylic acid being more preferred. The polymeric component formed from the unsaturated, acid-containing monomers may be grafted onto other types of polymer moieties such as starch or cellulose. Preferred absorbent gelling materials which can be prepared from conventional types of monomers include hydrolyzed acrylonitrile grafted starch, acrylic acid grafted starch, polyacrylates, maleic anhydride copolymers and combinations thereof, with polyacrylates and acrylic acid grafted starch being most preferred.

As shown best in FIG. 1, diaper 10 includes a pair of opposite waist panels 22, 23 interconnecting a crotch portion 24. Crotch portion 24 in turn includes a pair of opposite elasticized leg cuffs 25, 26. The waist panels 22, 23 are held together when diaper 10 is worn by a user by a fastening system which is illustrated in FIG. 1 as a pair of releasable tape tabs 27, 28.

Figure 3:
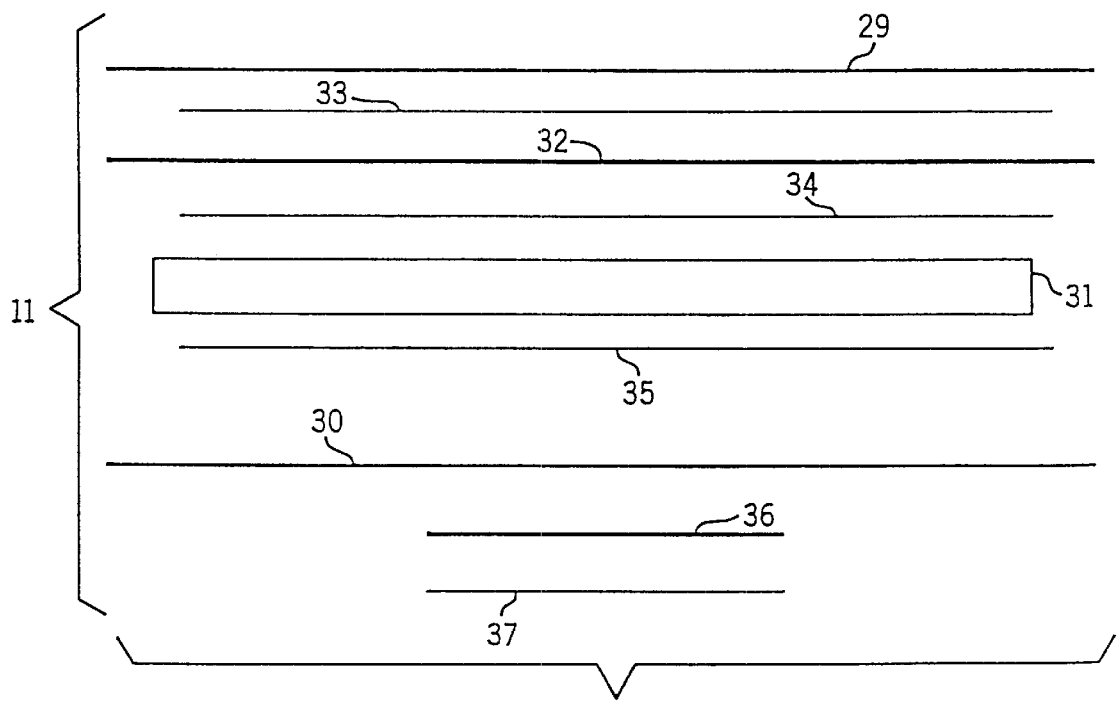
FIG. 3 is a schematic cross-sectional view of a disposable feminine care pad incorporating a hot melt adhesive constructed in accordance with the present invention.

Referring now to FIG. 3, there is illustrated an absorbent article illustrating a typical feminine care pad 11. Pad 11 comprises multiple layers of sheet material or substrates bonded together to form the absorbent article. More particularly, pad 11 includes a fluid pervious nonwoven topsheet 29 and a fluid impervious backsheet 30 (typically composed of a polyolefin material such as polyethylene or polypropylene) joined with topsheet 29. An absorbent core 31 is positioned between topsheet 29 and backsheet 30. Absorbent core 31 may be comprised of fluff and/or super absorbent (SAP) material. Fluff 8 is typically composed of absorbent fibers such as cellulose fibers, but may also include other absorbent natural or synthetic fibers and/or materials. Pad 11 may also include a top tissue layer 32 disposed between topsheet 29 and core 31. As shown in FIG. 3, one or more or all of the substrates may be bonded to an adjacent substrate by a layer of an adhesive formulated in accordance with the present invention. For example, nonwoven topsheet 29 is bonded to top tissue layer 32 by a layer of adhesive 33 applied to the underside of topsheet 29. In turn, top tissue layer 32 is bonded to core 31 by a layer of adhesive 34. Finally, core 31 is bonded to backsheet 30 by a layer of adhesive 35 applied to the upper surface of backsheet 30. The adhesive may be sprayed, spiral sprayed, melt blown, slot applied or may be applied as a bead depending upon the location and the type of bond desired. In the embodiment illustrated in FIG. 3, there is also a layer of adhesive 36 applied to the bottom side of backsheet 30 and release paper 37 covering adhesive 36. Thus, when paper 37 is removed to expose adhesive 36, adhesive layer 36 may be utilized to attach pad 11 to an undergarment worn by the user, as is conventional and well known in the art.

Figure 4:
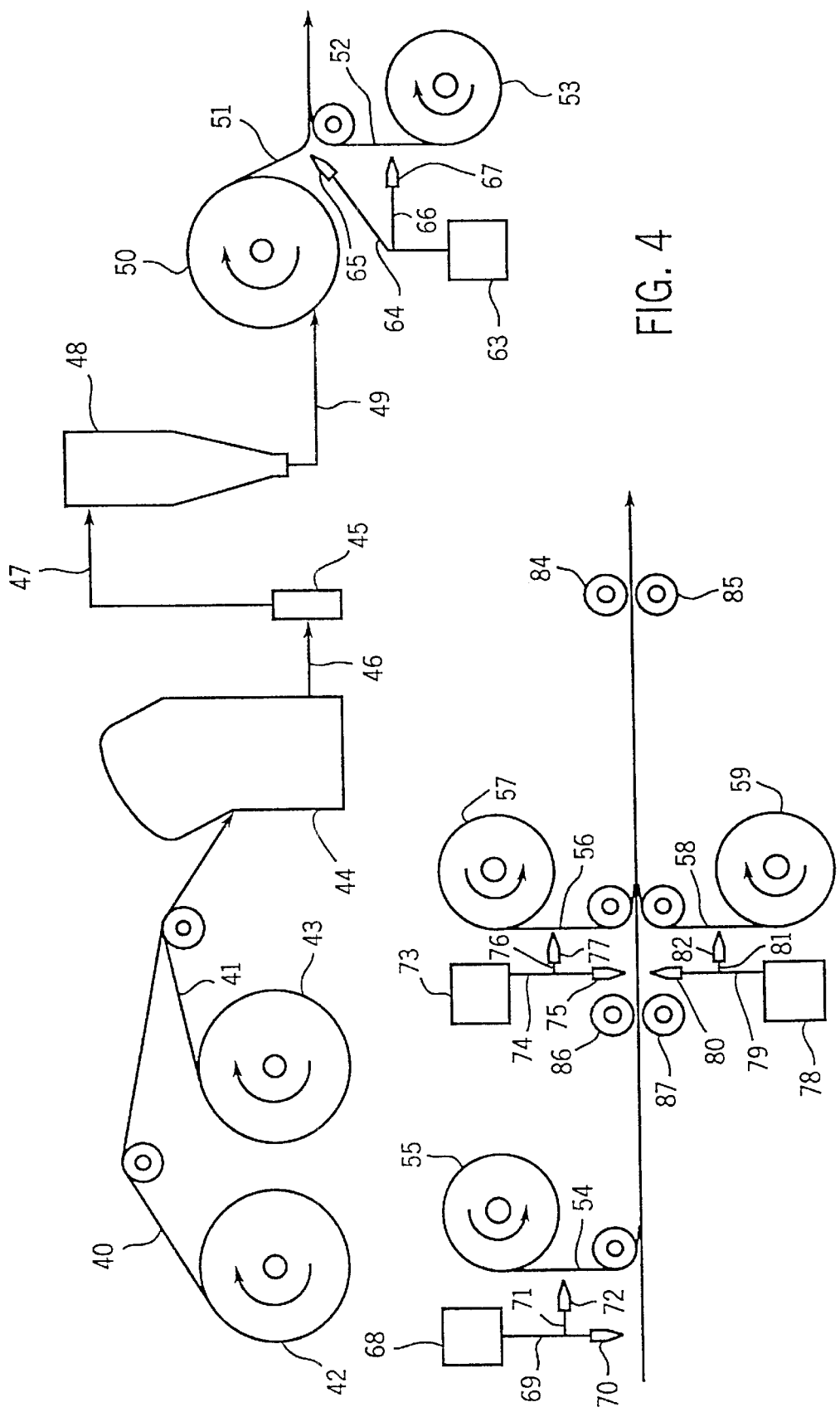
FIG. 4 is a schematic illustration of a system for manufacturing disposable feminine care pads utilizing the hot melt adhesive of the present invention.

Referring now to FIG. 4, there is schematically illustrated a system for manufacturing disposable feminine care pads which embodies the method of the present invention. More specifically, sheets 40 and 41 of absorbent material, typically compacted cellulose fibers, are fed from storage rolls 42 and 43 respectively into a hammermill 44 which shreds the sheets 40 and 41 to form fluff. The fluff is then air conveyed via blower 45 through lines 46 and 47 into a cyclone 48 which homogeneously mixes the fluff with air. The fluff and air mixture is then fed via line 49 to a roll 50 which forms the fluff into an absorbent core. As is conventional, roll 50 includes a screen which has the preformed shape of the core formed therein, and the interior of roll 50 is subjected to a vacuum which draws the fluff from line 49 onto the screen to form the core. As roll 50 rotates, a portion of the interior eventually becomes subject to positive pressure which results in the core being "blown off" the surface of the screen. At this time, the core is substantially non-self-supporting and thus, needs to be supported by a substrate. When making feminine care products such as sanitary napkins, core 51 is supported by a tissue substrate 52 which is fed from storage roll 53. The core 51 supported by tissue layer 52 is then fed downstream where a second tissue layer 54 being fed from drum 55 is applied to the upper surface of core 51. Finally, a nonwoven topsheet 56 fed from roll 57 is applied over tissue layer 54, and an impervious backsheet 58 fed from roll 59 is applied over tissue layer 52 to form the laminated structure illustrated in FIG. 3. The laminated structure is then fed downstream to be further processed into a sanitary napkin. Likewise, if the schematic illustration of the system illustrated in FIG. 4 is utilized to produce diapers, the laminate structure is also fed downstream to be further processed into the diaper illustrated in FIGS. 1 and 2.

The system illustrated in FIG. 4 and described up to this point is conventional and in standard use in the manufacture of feminine care pads and diapers. What is not standard or conventional, however, is the use of adhesives formulated in accordance with the present invention in the process described and illustrated in FIG. 4 to bond various components and substrates together. More specifically, in one embodiment, the present method provides a method of bonding the absorbent core to another substrate. In this embodiment, an adhesive formulated in accordance with the present invention may be sprayed from a source 63 via line 64 and nozzle 65 onto the bottom surface of core 51. Thereafter, when core 51 is joined with tissue layer 52 and subjected to pressure applied thereto when passing through a nip formed between rolls 86 and 87, the adhesive bonds tissue layer 52 to the interior surface of core 51. Alternately, tissue layer 52 may be bonded to core 51 by spraying the adhesive onto the interior surface of tissue layer 52 via line 66 and nozzle 67. Then, the core 51 and tissue layer 52 may be bonded together as they are subjected to the pressure applied by rolls 86 and 87.

Tissue layer 54 may also be bonded to the top surface of core 51 in a similar manner. As shown in FIG. 4, an adhesive from a source 68 formulated in accordance with the present invention may be applied to the top surface of core 51 via line 69 and nozzle 70. Thereafter, tissue layer 54 is applied to core 51 and when subjected to the pressure applied by rolls 86 and 87, the adhesive will result in a strong bond between tissue layer 54 and core 51. Alternately, the same bonding result can be accomplished by spraying adhesive from source 68 via line 71 and nozzle 72 onto the interior surface of tissue layer 54. Once applied, the adhesive will bond tissue layer 54 to the top side of core 51. In either case, the laminate structure is then passed through the nip formed between two rolls 86 and 87 which applies pressure against the laminate structure to ensure strong bonding between the substrates.

Finally, as illustrated, the nonwoven topsheet 56 and the impervious backsheet 58 may also be bonded utilizing adhesives formulated in accordance with the present invention. As illustrated, the topsheet 56 may be bonded to tissue layer 54 via adhesive fed from source 73 through line 74 and nozzle 75 onto the outer or top surface of tissue layer 54. Alternately, the adhesive from source 73 may be fed via line 76 and nozzle 77 onto the interior surface of nonwoven layer 56. Likewise, impervious backsheet 58 may be bonded to the underside of tissue layer 52 in a similar manner. An adhesive from source 78 formulated in accordance with the present invention may be fed via line 79 and nozzle 80 to be sprayed onto the lower surface of tissue layer 52. Alternately, the adhesive may be sprayed via line 81 and nozzle 82 onto the interior surface of backsheet 58.

Once joined into a laminate structure as illustrated in FIG. 3, the core 51, tissue layers 52 and 54, topsheet 56 and backsheet 58 are all subjected to pressure to bond these substrates together. This laminate structure is then passed through the nip formed between two calendar rolls 84 and 85 which applies pressure against the laminate structure to ensure strong bonding between all of the substrates. Thereafter, the laminate structure is fed downstream for further processing into the desired finished article, i.e. a feminine care pad or diaper or the like.

The invention is further illustrated by way of the examples which are set forth below:

EXAMPLE 1

Objective:

The scope of this Example is to investigate whether triclosan can be incorporated into a hot melt adhesive in order to provide an anti-microbial feature to disposable products. Irgasan PA® is a triclosan manufactured by CIBA and was used as the bacteriostat.

Test Methods/Results:

Two hot melt adhesives were selected to blend with a small percentage of triclosan. One is a water dispersible adhesive available from Ato Findley, Inc. and is designated H9548. This adhesive is based on a sulfonated polyester which is available from Eastman Chemical. A more detailed description of the polymer can be found in U.S. Pat. Nos. 4,910,292, 4,973,656 and 4,990,593. Recently, improved sulfonated polyesters were developed (Miller, et al WO 95/181891) which are characterized by reduced Tg's by the incorporation of branching.

The second product was a standard diaper construction adhesive available from Ato Findley, Inc., designated H2543. This product is based on a high styrene SIS (styrene-isoprene-styrene) block copolymer. A more detailed description of this type of adhesive can be found in U.S. Pat. No. 5,149,741.

A control mix, a mix with 0.5% triclosan, and a mix with 0.75% triclosan, were made of each product at 300° F. Each of the adhesives were applied at 300° F. to a standard 15.3 grams/m$^2$ (gsm) nonwoven substrate on the CT225 coater using a Nordson Control Weave applicator at 0.5 inch wide. The adhesive add-on level was 3 gsm. The pattern was fiberized. The nonwoven/adhesive was combined to release paper for easy removal for testing.

Ready-made petri plates of agar were used for this experiment. Inoculates were prepared using a barium sulfate standard for a turbidity of 150,000,000 bacteria/ml. The plates were inoculated using a sterile swab by streaking bacteria in three directions (to ensure complete coverage). A midline was drawn on each plate with a marker. To one side a piece of nonwoven (0.5×1.0") was set on the inoculated plate. A sample of nonwoven with adhesive was positioned on the other half. The plates were incubated at 35±2° C. for 24 hours and observed for areas of non-growth. Photographs were taken using a digital camera. The following table outlines the samples tested and the results for each bacteria type.

TABLE 1

Bacterial Growth Testing for Adhesives Blended with Triclosan vs. Non-Triclosan Controls

| Adhesive | Gram Positive Bacteria | Gram Negative Bacteria |
| --- | --- | --- |
| 1. Control nonwoven without adhesive | Complete growth over entire plate | Complete growth over entire plate |
| Nonwoven with adhesive H9548 (control no triclosan) | Complete growth over entire plate | Complete growth over entire plate |
| 2. Control nonwoven without adhesive | Complete growth over entire plate | Complete growth over entire plate |
| Nonwoven with adhesive H9548 w/0.5% triclosan | Area of non-growth present around nonwoven | Complete growth over entire plate |
| 3. Control nonwoven without adhesive | Complete growth over entire plate | Complete growth over entire plate |
| Nonwoven with adhesive H9548 w/0.75% triclosan | Area of non-growth present around nonwoven | Complete growth over entire plate |
| 4. Control nonwoven without adhesive | Complete growth over entire plate | Complete growth over entire plate |
| Nonwoven with adhesive H2543 (control no triclosan) | Complete growth over entire plate | Complete growth over entire plate |
| 5. Control nonwoven without adhesive | Complete growth over entire plate | Complete growth over entire plate |
| Nonwoven with adhesive H2543 w/0.5% triclosan | Area of non-growth present around nonwoven | Complete growth over entire plate |
| 6. Control nonwoven without adhesive | Complete growth over entire plate | Complete growth over entire plate |
| Nonwoven with adhesive H2543 w/0.75% triclosan | Area of non-growth present around nonwoven | Complete growth over entire plate |

Conclusion:

Both the water dispersible and the SIS construction hot melt adhesive products offered a bacteriostatic feature when the triclosan was blended at 0.5 and 0.75%. A larger area of non-growth was present on the samples with the higher level of triclosan.

Because triclosan is a broad-spectrum bacteriostat, it was thought that it would work on both the gram positive and the gram-negative strains. The bacteria strains used in Table 1 were not specifically identified, but the gram-positive cocci used are similar to a Staphylococcus type and the gram-negative rods are similar to Escherichia coli (E. coli). The bacteriostat was effective at inhibiting the growth of the gram-positive bacteria used in this experiment, but not the gram-negative strain. With this in mind, the next steps would be to obtain strains of gram-positive and gram-negative bacteria known to be present in the digestive tract or on the skin such as Bacillus pasteurii, Proteus vulgaris, and Proteus mirabilis. These bacteria are known to breakdown urea into ammonia. The test described can be used to determine if triclosan is effective at inhibiting the growth of these types of bacteria.

EXAMPLE 2

Additional testing was conducted to further investigate whether anti-microbial agents incorporated into adhesives are effective at inhibiting the growth of bacteria. Two antimicrobials, chlorophene (2-benzyl-4-chlorophenol 95%) and triclosan (2,2,4'-trichloro-2'-hydroxyphenyl ether), were each incorporated into two different adhesives, H9548 (copolyester based water-soluble hot melt) and H2543 (SIS based construction hot melt) at 0.5% and 0.75%. These formulations along with controls of each without antimicrobial added were fiberized onto a standard 15.3 gsm nonwoven at a coating weight of 3 gsm. A total of 11 samples, including a roll of neat nonwoven, were submitted for testing.

The screening test used to evaluate use effectiveness of the adhesives containing antimicrobial agents was modeled after the standard disc-agar diffusion method used for antimicrobial susceptibility testing of clinical bacterial isolates. Three known strains of bacteria were used for testing: Staphylococcus aureus (ATCC #25923), Escherichia coli (ATCC #25922), and Proteus mirabilis (ATCC #7002). Staph aureus is typically found on the skin. E. coli and Proteus species are inhabitants of the human intestinal tract. Proteus mirabilis is further distinguished by the fact that it possess the urease enzyme, which can hydrolyze urea to ammonia. A standardized inoculum was prepared by transferring bacterial colonies from a 24 hour culture to a tube containing about 5 mls of 0.85% NaCl (physiological or normal saline) to match the turbidity of a 0.5 McFarland standard (barium sulfate). This controls the size of the inoculum to be approximately 1.5×10$^6$ bacteria/ml.

A sterile swab was used to apply the standardized bacterial suspension to Mueller Hinton II agar plates. To ensure even distribution of the inoculum, the entire plate is streaked three times, rotating approximately 60° each time. Discs of each of the coated adhesives and the nonwoven control, about 21.4 mm in diameter, were cut from the roll stock with efforts to minimize the introduction of extraneous bacteria contamination. These discs were placed onto the agar surface and lightly pressed in place to ensure good contact. Plates were incubated overnight at 35° C. and observed for any zone of inhibition of bacterial growth. Inhibition zone diameters were measured to establish a relative comparison of antimicrobial effectiveness.

Results show that only the triclosan containing adhesives exhibit some ability to inhibit bacterial growth. In addition, the effectiveness of the triclosan is greater with the H2543 compared to the H9548, as indicated by the larger zone sizes. Since the principle of this test relies on the diffusion of the antimicrobial out of the sample disc and into the agar, it can be theorized that triclosan is able to diffuse out of the H2543 more readily than out of the H9548. The reason for this is not known but one possible theory could be solubility. Triclosan is an ether that is practically insoluble in water. The copolyester component in H9548 is only marginally soluble in THF, a water miscible ether. Therefore, the triclosan and the copolyester are compatible with each other so that the triclosan does not bloom or diffuse readily to the surface of that composition. In all cases but one, the zone of inhibition is larger with the 0.75% triclosan versus the 0.5%. This may again be related to the diffusion factor in that the zone size of the *Staph aureus* is already quite large and the logistics of the test may not allow for further diffusion.

TABLE 2

Comparison of Bacteriostats for Controlling Known Bacteria

| | S. aureus (25923) | E. coli (25922) | P. mirabilis (7002) |
|---|---|---|---|
| nonwoven control | no zone of inhibition | no zone of inhibition | no zone of inhibition |
| H9548 control | no zone of inhibition | no zone of inhibition | no zone of inhibition |
| H2543 control | no zone of inhibition | no zone of inhibition | no zone of inhibition |
| H9548 with 0.5% chlorophene | no zone of inhibition | no zone of inhibition | no zone of inhibition |
| H9548 with 0.75% chlorophene | no zone of inhibition | no zone of inhibition | no zone of inhibition |
| H2543 with 0.5% chlorophene | no zone of inhibition | no zone of inhibition | no zone of inhibition |
| H2543 with 0.75% chlorophene | no zone of inhibition | no zone of inhibition | no zone of inhibition |
| H9548 with 0.5% triclosan | 32.04 mm | no zone of inhibition | no zone of inhibition |
| H9548 with 0.75% triclosan | 35.37 mm | no zone of inhibition | no zone of inhibition |
| H2543 with 0.5% triclosan | 40.00 mm | 23.74 mm | 25.53 mm |
| H2543 with 0.75% triclosan | 40.51 mm | 25.41 mm | 27.66 mm |

We claim:

1. An antimicrobial hot melt adhesive composition, comprising a blend of the following components:

about 10–80% of a polymer;
   about 20–70% of a tackifying resin;
   about 0–50% of a plasticizer;
   about 0–50% of a wax;
   about 0.1–5% of an antioxidant; and
   about 0.01–5% of a bacteriostat, the components totaling 100% by weight, and said bacteriostat comprising a compound of the formula:

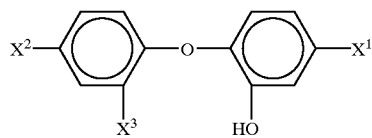

wherein $X^1$ is a member selected from the group consisting of chlorine and bromine, $X^2$ is a member selected from the group consisting of chlorine and bromine, and $X^3$ is a member selected from the group consisting of hydrogen and chlorine.

2. The composition of claim 1, wherein each of $X^1$, $X^2$ and $X^3$ represents chlorine.

3. The composition of claim 1, wherein each of $X^1$ and $X^2$ represents chlorine, and $X^3$ represents hydrogen.

4. The composition of claim 1 containing 0.1% to 4% by weight of said bacteriostat.

5. The composition of claim 1 containing 0.3% to 2% by weight of said bacteriostat.

6. The composition of claim 1 containing about 0.5% of the bacteriostat.

7. The composition of claim 1 containing about 0.75% of the bacteriostat.

8. The composition of claim 1 wherein the polymer is a sulfonated polyester.

9. The composition of claim 1 wherein the polymer is selected from the group consisting of ethylene/vinyl acetate, ethylene acrylate, ethylene methacrylate, ethylene methyl acrylate, ethylene methyl methacrylate, high density polyethylene, low density polyethylene, polyethylene blends, chemically modified polyethylene, copolymers of ethylene and 1–6 mono- or di-unsaturated monomers, ethylene/styrene interpolymers, polyesters, amorphous polyalphaolefins, metallocene catalyzed polyalphaolefins, styrene-isoprene-styrene block copolymer, styrene-butadiene-styrene block copolymer, styrene-ethylene-butylene-styrene block copolymer, styrene-butadiene-rubber, acrylic polymers and copolymers, styrene acrylic polymers and copolymers; polybutene-1 homopolymers and copolymers, linear A-B-A block, linear A-(B-A)$_n$-B multi-block copolymers, and radial or teleblock copolymers of the formula (A-B)$_n$-Y wherein A comprises a polystyrene block, B comprises a substantially rubbery polybutadiene or polyisoprene block, Y comprises a multivalent compound, and n is an integer of at least 3, and mixtures of said substances.

10. The composition of claim 1 wherein the polymer is a water soluble polymer.

11. The composition of claim 10 wherein the water soluble polymer is selected from the group consisting of sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, and polyvinylpyrrolidone/vinyl acetate.

12. The composition of claim 1 wherein the antioxidant is a hindered phenol.

13. The composition of claim 1 wherein the tackifying resin is selected from the group consisting of aliphatic and cycloaliphatic hydrocarbon resins and their hydrogenated derivatives, aromatic and hydrogenated aromatic hydrocarbon resins, aromatically modified aliphatic and cycloaliphatic resins and their hydrogenated derivatives, natural and modified rosins, esters of natural and modified rosins, polyterpenes, copolymers and terpolymers of natural terpenes and phenolic modified terpenes.

14. The composition of claim 1 wherein the plasticizer is selected from the group consisting of mineral oil and polybutene.

15. The composition of claim 1 wherein the wax is selected from the group consisting of low molecular weight polyethylene, petroleum waxes, synthetic waxes and polyolefin waxes.

16. The composition of claim 1 wherein the adhesive composition further includes a filler in the amount up to 50% by weight.

17. The composition of claim 16 wherein said filler is selected from the group consisting of talc, calcium carbonate, clay, silica, mica, wollastonite, feldspar, aluminum silicate, alumina, hydrate alumina, glass microspheres, ceramic microspheres, thermoplastic microspheres, baryte and wood flour.

18. The composition of claim 1 wherein the adhesive composition further includes an additive selected from the group consisting of a colorant and a fluorescent agent.

19. An antimicrobial hot melt adhesive composition, comprising a blend of the following components;
    about 20–35% of a polymer;
    about 35–60% of a tackifying resin;
    about 5–40% of a plasticizer;
    about 0–50% of a wax;
    about 1% of an antioxidant; and
    about 0.3–2% of a bacteriostat;
    the components totaling 100% by weight; and
    said bacteriostat comprising a compound of the formula:

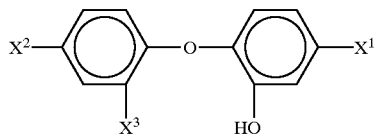

wherein $X^1$ is a member selected from the group consisting of chlorine and bromine, $X^2$ is a member selected from the group consisting of chlorine and bromine, and $X^3$ is a member selected from the group consisting of hydrogen and chlorine.

20. The composition of claim 19 wherein each of $X^1$, $X^2$ and $X^3$ represents chlorine.

21. The composition of claim 19 wherein each of $X^1$ and $X^2$ represents chlorine, and $X^3$ represents hydrogen.

22. The composition of claim 19 wherein the polymer is selected from the group consisting of ethylene/vinyl acetate, ethylene acrylate, ethylene acrylate, ethylene methacrylate, ethylene methyl acrylate, ethylene methyl methacrylate, high density polyethylene, low density polyethylene, polyethylene blends, chemically modified polyethylene, copolymers of ethylene and 1–6 mono- or di-unsaturated monomers, ethylene/styrene interpolymers, polyesters, amorphous polyalphaolefins, metallocene catalyzed polyalphaolefins, styrene-isoprene-styrene block copolymer, styrene-butadiene-styrene block copolymer, styrene-ethylene-butylene-styrene block copolymer, styrene-butadiene-rubber, acrylic polymers and copolymers, styrene acrylic polymers and copolymers; polybutene-1 homopolymers and copolymers, linear A-B-A block, linear A-(B-A)$_n$-B multiblock copolymers, and radial or teleblock copolymers of the formula (A-B)$_n$-Y wherein A comprises a polystyrene block, B comprises a substantially rubbery polybutadiene or polyisoprene block, Y comprises a multivalent compound, and n is an integer of at least 3, and mixtures of said substances.

23. The composition of claim 19 wherein the polymer is a water soluble polymer.

24. The composition of claim 23 wherein the water soluble polymer is selected for the group consisting of sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, and polyvinylpyrrolidone/vinyl acetate.

25. The composition of claim 19 wherein the antioxidant is a hindered phenol.

26. The composition of claim 19 wherein the tackifying resin is selected from the group consisting of aliphatic and cycloaliphatic hydrocarbon resins and their hydrogenated derivatives, aromatic and hydrogenated aromatic hydrocarbon resins, aromatically modified aliphatic and cycloaliphatic resins and their hydrogenated derivatives, natural and modified rosins, esters of natural and modified rosins, polyterpenes, copolymers and terpolymers of natural terpene and phenolic modified terpenes.

27. The composition of claim 19 wherein the plasticizer is selected from the group consisting of mineral oil and polybutene.

28. The composition of claim 19 wherein the wax is selected from the group consisting of low molecular weight polyethylene, petroleum waxes, synthetic waxes and polyolefin waxes.

29. The composition of claim 19 wherein the adhesive composition further includes a filler in the amount up to 50% by weight.

30. The composition of claim 29 wherein said filler is selected from the group consisting of talc, calcium carbonate, clay, silica, mica, wollastonite, feldspar, aluminum silicate, alumina, hydrate alumina, glass microspheres, ceramic microspheres, thermoplastic microspheres, baryte and wood flour.

31. The composition of claim 19 wherein the adhesive composition further includes an additive selected from the group consisting of a colorant and a fluorescent agent.

32. An absorbent article containing the adhesive of claim 1.

33. The absorbent article of claim 32 comprising a disposable diaper.

34. The absorbent article of claim 32 comprising a feminine care product.

35. The absorbent article of claim 32 comprising a surgical drape.

36. An antimicrobial, sprayable, thermoplastic polymer composition, comprising:
    about 95–99.99% by weight of a thermoplastic polymer, said thermoplastic polymer having a melt index greater than about 100; and
    about 0.01–5% by weight of a bacteriostat; and where the composition has a viscosity of less than about 50,000 cP at 350° F.

37. The composition of claim 36 wherein said bacteriostat comprises a compound of the formula:

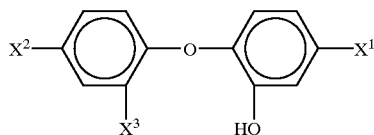

wherein $X^1$ is a member selected from the group consisting of chlorine and bromine, $X^2$ is a member selected from the group consisting of chlorine and bromine, and $X^3$ is a member selected from the group consisting of hydrogen and chlorine.

38. The composition of claim 37, wherein each of $X^1$, $X^2$ and $X^3$ represents chlorine.

39. The composition of claim 37, wherein each of $X^1$ and $X^2$ represents chlorine, and $X^3$ represents hydrogen.

40. The composition of claim 36 containing 0.1% to 4% by weight of said bacteriostat.

41. The composition of claim 36 containing 0.3% to 2% by weight of said bacteriostat.

42. The composition of claim 36 containing about 0.5% of the bacteriostat.

43. The composition of claim 36 containing about 0.75% of the bacteriostat.

44. The composition of claim 36 wherein the polymer is selected from the group consisting of ethylene/vinyl acetate, ethylene acrylate, ethylene methacrylate, ethylene methyl acrylate, ethylene methyl methacrylate, high density polyethylene, low density polyethylene, polyethylene blends, chemically modified polyethylene, copolymers of ethylene and 1–6 mono- or di-unsaturated monomers, ethylene/styrene interpolymers, polyesters, amorphous polyalphaolefins, metallocene catalyzed polyalphaolefins, styrene-isoprene-styrene block copolymer, styrene-butadiene-styrene block copolymer, styrene-ethylene-butylene-styrene block copolymer, styrene-butadiene-rubber, acrylic polymers and copolymers, styrene acrylic polymers and copolymers; polybutene-1 homopolymers and copolymers, linear A-B-A block, linear A-(B-A)$_n$-B multi-block copolymers, and radial or teleblock copolymers of the formula (A-B)$_n$-Y wherein A comprises a polystyrene block, B comprises a substantially rubbery polybutadiene or polyisoprene block, Y comprises a multivalent compound, and n is an integer of at least 3, and mixtures of said substances.

45. The composition of claim 36 wherein the polymer is a water soluble polymer.

46. The composition of claim 45 wherein the water soluble polymer is selected from the group consisting of sulfonated polyesters, polyvinyl methyl ether, polyalkyleneimine polymers and copolymers, polyvinyl alcohol, polylactide polymers, polyethylene glycol polymers, polyacrylic acid and salts thereof, ethylene/acrylic acid and salts thereof, and polyvinylpyrrolidone/vinyl acetate.

47. The composition of claim 36 wherein said polymer has a melt index greater than about 500.

48. The composition of claim 36 wherein said polymer has a melt index greater than about 1000.

49. The composition of claim 47 wherein said viscosity is less than 20,000 cP.

50. The composition of claim 48 wherein said viscosity is less than 10,000 cP.

51. An absorbent article containing the polymer composition of claim 36.

52. The absorbent article of claim 51 comprising a disposable diaper.

53. The absorbent article of claim 51 comprising a feminine care product.

54. The absorbent article of claim 51 comprising a surgical drape.

* * * * *